US005733535A

United States Patent [19]
Hollingshead et al.

[11] Patent Number: 5,733,535
[45] Date of Patent: Mar. 31, 1998

[54] TOPICAL COMPOSITIONS CONTAINING N-ACETYLCYSTEINE AND ODOR MASKING MATERIALS

[75] Inventors: Judith Ann Hollingshead, Batavia; Larry Richard Robinson, Lebanon, both of Ohio

[73] Assignee: The Procter & Gamble Co., Cincinnati, Ohio

[21] Appl. No.: 548,223

[22] Filed: Oct. 25, 1995

[51] Int. Cl.$^6$ .............. A61K 7/32; A61K 7/46; A61K 31/24; A61K 7/00
[52] U.S. Cl. .............. 424/65; 424/66; 424/67; 424/68; 424/400; 424/401; 512/1; 514/532
[58] Field of Search .............. 424/65, 400, 401, 424/66, 67, 68; 512/1; 514/532

[56] References Cited

U.S. PATENT DOCUMENTS 5,296,500   3/1994   Hillebrand .............. 514/562

*Primary Examiner*—Shelley A. Dodson
*Attorney, Agent, or Firm*—David L. Suter; David K. Dabbiere; William J. Winter

[57] ABSTRACT

Disclosed are topical compositions comprising from about 0.01% to about 50% by weight of N-acetylcysteine or related compounds, from about 0.01% to about 0.5% by weight of selected combinations of certain perfume chemicals to effectively mask malodors associated with topical application of the N-acetylcysteine or related compounds on skin; and a cosmetically acceptable topical carrier. These topical compositions are useful for visibly improving the appearance of skin.

18 Claims, No Drawings

TOPICAL COMPOSITIONS CONTAINING N-ACETYLCYSTEINE AND ODOR MASKING MATERIALS

FIELD OF THE INVENTION

The present invention relates to topical compositions comprising N-acetylcysteine or related compounds, and selected combinations of certain perfume chemicals as an odor masking material.

BACKGROUND OF THE INVENTION

Many personal care products currently available to consumers are directed primarily to improving the health and/or physical appearance of the skin. Among these skin care products, many are directed to delaying, minimizing or even eliminating skin wrinkling and other histological changes typically associated with the natural aging of human skin.

Human skin is subject to abuse by many extrinsic and intrinsic factors. Extrinsic factors include ultraviolet radiation, wind, low humidity, harsh surfactants, abrasives, and the like. Intrinsic factors include chronological aging and other biochemical changes from within the skin. The aging process in particular results in the thinning and general degradation of skin. As the skin naturally ages, there is a reduction in the cells and blood vessels that supply the skin, and flattening of the dermal-epidermal junction which results in weaker mechanical resistance of this junction. Whether extrinsic or intrinsic, these abuse factors often result in undesirable wrinkling and other histological changes of the skin.

Various products have been developed in attempts to minimize or eliminate the wrinkling and other histological changes associated with aging or exposure to various harsh extrinsic factors. Examples of such products include moisturizers and topical formulations containing N-acetylcysteine, retinoids (e.g., retinoic acid), alpha-hydroxy acids (e.g., glycolic acid, lactic acid) and/or other similar materials.

Although topical products containing N-acetylcysteine are especially effective for this purpose, their use has been limited. During formulation, packaging and storage of these products, some of the N-acetylcysteine typically degrades into and releases malodorous thiols and hydrogen sulfide. The formation of these malodorous compounds has thus limited the use of topical compositions containing N-acetylcysteine, especially when such compositions are intended for facial application. Attempts to minimize or eliminate these malodors have included the use of various perfumes and fragrances, and the use of various chelating agents, e.g., zinc salts.

Most perfumes, however, do not adequately mask the malodors associated with these topical products. Although the overall sensory impression may change in these perfumed formulations, there remains a distinct and undesirable maledor arising from the N-acetylcysteine and its thiol and hydrogen sulfide degradation products.

It has now been found that even the use of conventional chelating agents, e.g., zinc salts, to control malodors does not adequately control such odors once these topical products are applied to skin. These chelating agents minimize malodors generated from within the packaged compositions, and thus minimize development of malodors within the package headspace and within the composition itself prior to application to the skin. However, once the composition is applied to the skin, the malodors are substantially enhanced. Moreover, Applicants have found that neither conventional perfumes nor conventional chelating agents adequately eliminate or mask these enhanced aromas arising after topical application of the compositions to human skin.

Applicants have found that select combinations of certain perfume chemicals, when incorporated into N-acetylcysteine compositions, effectively mash the enhanced malodors generated from topical application of such compositions onto human skin.

Given the forgoing, there remains a need to provide topical compositions containing N-acetylcysteine which emit an acceptable aroma, especially when applied topically. It is therefore an object of the present invention to provide such compositions, and specifically to provide topical compositions containing N-acetylcysteine which have an acceptable aroma prior to and after application to the skin, and more specifically to provide such compositions comprising effective odor masking materials.

SUMMARY OF THE INVENTION

The present invention relates to topical compositions comprising from about 0.01% to about 50% by weight of a compound selected from the group consisting of N-acetylcysteine, derivatives of N-acetylcysteine, pharmaceutically-acceptable salts of N-acetylcysteine, pharmaceutically-acceptable salts of derivatives of N-acetylcysteine, and mixtures thereof;

from about 0.01% to about 0.5% by weight of an odor masking material selected to cover malodor on the skin associated with topical application of said compound, and a topical carrier. The odor masking material in turn comprises the following combination of perfume chemicals:

(i) from about 35% to about 95% by weight of aromatic ester, aliphatic ester or mixtures thereof, having an average molecular weight of from about 120 to about 205;

(ii) from about 4% to about 60% by weight of aromatic alcohol, aliphatic alcohol, or mixtures thereof, having an average molecular weight of from about 110 to about 180;

(iii) from about 0.05% to about 20% by weight of aliphatic ketones having an average molecular weight of less than about 210;

(iv) from about 0.1% to about 20% by weight of aromatic aldehydes, aliphatic aldehydes or mixtures thereof, having an average molecular weight of from about 100 to about 225;

(v) not more than about 20% by weight of perfume chemicals selected from the group consisting of aromatic ether, aliphatic ether, aliphatic ester, aromatic ester, or mixtures thereof, having an average molecular weight of at least about 210.

DETAILED DESCRIPTION OF THE INVENTION

The topical compositions of the present invention comprise N-acetylcysteine and selected combinations of certain perfume chemicals, all incorporated into a cosmetically acceptable carrier. These compositions are preferably leave-on formulations, and are useful for treating and visibly improving the appearance of human skin.

The composition of the present invention can comprise, consist of, or consist essentially of, the essential as well as optional components described herein.

As used herein, all parts, percentages and ratios are by weight of the total composition and all measurements are made at 25° C., unless otherwise specified. All weight percentages are on an actives weight basis, unless otherwise specified.

"Topical application" as used herein means to apply or spread the compositions of the present onto the surface of the human skin.

"Cosmetically- and/or pharmaceutically-acceptable" as used herein refers to materials that are suitable for use in contact with the tissues of humans and lower animals without undue toxicity, incompatibility, instability, irritation, allergic response and the like.

"Treating and visibly improving the appearance of human skin" as used herein means that the compositions of the present invention are useful for topical application and provide benefits such as ameliorating the signs of skin aging, improving the texture of the skin, providing a depilatory effect for removing unwanted hair, decreasing pore size, and/or providing a skin lightening benefit on hyperpigmented spots and the like.

"Signs of skin aging" as used herein refers to outwardly visible and tactilely perceptible manifestations, all internal manifestations, as well as any other macro or micro effects. For example, the term "skin aging" as used herein includes processes whether induced or caused by extrinsic factors or intrinsic factors. These processes include, but are not limited to the development of wrinkles, including both fine superficial wrinkles and coarse deep wrinkles, skin lines, sagging, discoloration, age spots, keratoses, hyperkeratinization, elastosis, collagen breakdown, and other histological changes in the stratum corneum, dermis, epidermis, the vascular system, and underlying tissues.

"N-acetylcysteine" as used herein, unless otherwise specified, includes N-acetylcysteine, N-acetyl-L-cysteine, N-acetyl-D-cysteine, pharmaceutically acceptable derivatives thereof, pharmaceutically-acceptable salts thereof, and mixtures thereof.

N-acetylcysteine

The compositions of the present invention comprise a compound selected from the group consisting of N-acetylcysteine, N-acetyl-L-cysteine, N-acetyl-D-cysteine, pharmaceutically acceptable derivatives thereof, pharmaceutically-acceptable salts thereof, and mixtures thereof, preferably N-acetyl-L-cysteine. Concentrations of these compounds range from about 0.01% to about 50%, more preferably from about 0.1% to about 10%, and most preferably from about 0.25% to about 5%, by weight of the composition.

N-acetylcysteine can be represented by the following chemical structure:

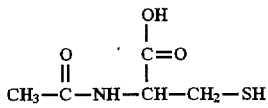

N-acetylcysteine is an "acetylated" derivative of the amino acid cysteine. Cysteine, and all amino acids more complex than glycine, exists as two enantiomeric forms, the naturally occurring "L" form and its non-naturally occurring "D" form. The "L" form of N-acetylcysteine, which is designated N-acetyl-L-cysteine, is preferred for use herein, because it is more readily available, although the "D" form can be used. It is also recognized that cysteine and its N-acetylated derivative can exist as an oxidized dimer, however, the monomeric form of N-acetylcysteine is preferred for use herein.

Also useful herein are derivatives of N-acetylcysteine. These derivatives include esters, amides, anhydrides, and thio-esters and thio-ethers of the sulfhydryl moiety. Non-limiting examples of these derivatives include: methyl N-acetylcysteine, ethyl N-acetylcysteine, stearyl N-acetylcysteine, N-acetylcysteine methylthioether, N,S-diacetylcysteine, N-acetylcysteine amide, and the mixed anhydride of N-acetylcysteine and acetic acid.

Also useful herein are pharmaceutically-acceptable salts of N-acetylcysteine and salts of derivatives of N-acetylcysteine. Nonlimiting examples of these salts include sodium salts, potassium salts, magnesium salts, calcium salts, zinc salts, ammonium salts, alkyl ammonium and alkanol ammonium salts wherein the ammonium ion is substituted with one or more alkyl or alkanol moieties.

N-acetylcysteine and related compounds, salts and derivatives suitable for use in the compositions herein are described in The Merck Index, Tenth Edition, entry 82, page 13, (1983); and U.S. Pat. No. 5,296,500; which descriptions are incorporated herein by reference.

Odor Masking Materials

The compositions of the present invention comprise an odor-masking material which contains select combinations of certain perfume chemicals. Concentrations of the odor-masking material ranges from about 0.01% to about 0.5%, preferably from about 0.02% to about 0.3%, and more preferably from about 0.03% to about 0.2%, by weight of the compositions. The odor masking material comprises the following combination of perfume chemicals:

(a) from about 35% to about 95%, preferably from about 40% to about 85%, by weight of aromatic ester, aliphatic ester or mixtures thereof, having an average molecular weight of from about 120 to about 205, preferably from about 150 to about 200;

(b) from about 4% to about 60%, preferably from about 10% to about 50%, by weight of aromatic alcohol, aliphatic alcohol, or mixtures thereof, having an average molecular weight of from about 110 to about 180, preferably from about 120 to about 160;

(c) from about 0.05% to about 20%, preferably from about 0.1% to about 15%, by weight of aliphatic ketones, having an average molecular weight of less than about 210, preferably from about 160 to about 200;

(d) from about 0.1% to about 20%, preferably from about 0.2% to about 15%, by weight of aromatic aldehydes, aliphatic aldehydes or mixtures thereof, having an average molecular weight of from about 100 to about 225, preferably from about 130 to about 220;

(e) less than about 20%, preferably less than about 10%, most preferably less than about 5%, by weight of perfume chemicals selected from the group consisting of aromatic ether, aliphatic ether, aliphatic ester, aromatic ester, or mixtures thereof, having an average molecular weight of least about 210.

Specific examples of suitable and preferred perfume chemicals for use in the odor masking material of the composition include the following:

| Common Name | Chemical Type | Chemical Name | Approx. M.W. |
|---|---|---|---|
| adoxal | aliphatic aldehyde | 2,6,10-trimethyl-9-undecen-1-al | 210 |
| amyl acetate | ester | 3-methyl-1-butanol acetate | 130 |
| anisic aldehyde | aromatic aldehyde | 4-methoxy benzaldehyde | 136 |

-continued

| Common Name | Chemical Type | Chemical Name | Approx. M.W. |
|---|---|---|---|
| benzaldehyde | aromatic aldehyde | benzaldehyde | 106 |
| benzyl acetate | ester | benzyl acetate | 150 |
| benzyl butyrate | ester | benzyl butyrate | 178 |
| benzyl propionate | ester | benzyl propionate | 164 |
| beta damascone | aliphatic ketone | 1-(2,6,6-trimethyl-1-cyclohexen-1-yl)-2-butene-1-one | 192 |
| cis-3-hexenyl salicylate | ester | beta, gamma-hexenyl salicylate | 220 |
| citronellol | alcohol | 3,7-dimethyl-6-octenol | 156 |
| citronellyl acetate | ester | 3,7-dimethyl-6-octen-1-yl acetate | 198 |
| citronellyl nitrile | ester | 3,7-dimethyl-2,6-octadienenitrile | 151 |
| cymal | aromatic aldehyde | 2-methyl-3-(para iso propyl phenyl)propionaldehyde | 190 |
| decyl aldehyde | aliphatic aldehyde | decyl aldehyde | 156 |
| delta damascone | aliphatic ketone | 1-(2,6,6-trimethyl-3-cylco-hexen-1-yl)-2-buten-1-one | 192 |
| dihydromyrcenol | alcohol | 3-methylene-7-methyl octan-7-ol | 156 |
| ethyl vanillin | aromatic aldehyde | ethyl vanillin | 166 |
| florhydral | aromatic aldehyde | 3-(3-isopropylphenyl) butanal | 190 |
| geraniol | alcohol | 3,7-dimethyl-2,6-octadien-1-ol | 154 |
| geranyl acetate | ester | 3,7-dimethyl-2,6-octadien-1-yl acetate | 196 |
| geranyl formate | ester | trans 3,7-dimethyl-2,6-octadienyl formate | 182 |
| geranyl nitrile | ester | 3,7-dimethyl-2,6-octadienenitrile | 149 |
| helional | aromatic aldehyde | alpha-methyl-3,4,(methylenedioxy) hydrocinnamaldehyde | 192 |
| heliotropin | aromatic aldehyde | heliotropin | 150 |
| hexyl cinnamic aldehyde | aromatic aldehyde | alpha-n-hexyl cinnamic acid | 216 |
| hydroxycitronellal | aliphatic aldehyde | hydroxycitronellal | 172 |
| ionone alpha | aliphatic ketone | 4-(2,6,6-trimethyl-1-cyclohexenyl-1-yl)-3-buten-2-one | 192 |
| ionone beta | aliphatic ketone | 4-(2,6,6-trimethyl-1-cyclohexen-1-yl)-3-butene-2-one | 192 |
| koavone | aliphatic aldehyde | acetyl di-isoamylene | 182 |
| lauric aldehyde | aliphatic aldehyde | lauric aldehyde | 184 |
| linalyl acetate | ester | 3-hydroxy-3,7-dimethyl-1,6-octadiene acetate | 196 |
| linalyl butyrate | ester | linalyl-n-butyrate | 224 |
| linalyl propionate | ester | 3,7-dimethyl-1,6-octadien-3-yl propionate | 210 |
| lyral | aliphatic aldehyde | 4-(4-hydroxy-4-methyl-pentyl) 3-cylcohexene-1-carboxaldehyde | 210 |
| methyl anthranilate | aromatic amine | methyl-2-aminobenzoate | 151 |
| methyl nonyl acetaldehyde | aliphatic aldehyde | methyl nonyl acetaldehyde | 184 |
| P. T. bucinal | aromatic aldehyde | 2-methyl-3(para tert butylphenyl) propionaldehyde | 204 |
| phenyl acetaldehyde | aromatic aldehyde | 1-oxo-2-phenylethane | 120 |
| phenyl acetaldehyde dimethyl acetal | aromatic aldehyde | phenyl acetaldehyde dimethyl acetal | 166 |
| phenyl ethyl acetate | ester | phenyl ethyl acetate | 164 |
| phenyl ethyl alcohol | alcohol | phenyl ethyl alcohol | 122 |
| prenyl acetate | ester | 2-methylbuten-2-ol-4-acetate | 128 |
| terpineol (alpha terpineol and beta terpineol) | alcohol | para-menth-1-en-8-ol, para-menth-1-en-1-ol | 154 |
| undecyl aldehyde | aliphatic aldehyde | undecanal | 170 |
| undecylenic aldehyde | aliphatic aldehyde | undecylenic aldehyde | 168 |
| vanillin | aromatic aldehyde | 4-hydroxy-3-methoxybenzaldehyde | 152 |
| verdox | ester | 2-tert-butyl cyclohexyl acetate | 198 |
| vertenex | ester | 4-tertiary-butyl cyclohexyl acetate | 198 |

It has been found that the odor masking material described herein effectively covers or masks malodors associated with topical N-acetylcysteine compositions after application of such compositions onto human skin. Although these malodors arise primarily from volatile thiol and hydrogen sulfide degradation products found within the compositions, it is not fully understood why such thiol or hydrogen sulfide odors are enhanced or otherwise generated after application onto skin. It has also been found that the odor masking material described herein remains substantive to the skin for an amount of time effective to cover or mask the malodors emitted from the topically applied N-acetylcysteine composition. The odor masking materials can also act as a "scent signal" in the form of a pleasant odor which signals the masking of the malodor on the skin.

It has been found that many of the common perfume materials used in personal care products provide little or no odor masking benefits on skin when used in the compositions herein. Examples of such ineffective perfume materials include aromatic ketones, aromatic and aliphatic ethers, and lactones, all of which have molecular weights of greater than about 210, as well as aromatic and aliphatic esters having molecular weights greater than about 210. Specific examples of such ineffective perfume materials include ethylene brassylate, exaltolide, methyl dihydro jasmonate, galaxolide, tonalid/musk plus, musk indanone, and benzylsalicylate. Concentrations of these ineffective Perfume materials in the compositions herein are preferably minimized or avoided altogether, but in no event should such materials represent more than about 10%, preferably no more than about 5% by weigh of the composition.

Topical Carrier

The compositions of the present invention comprise a cosmetically acceptable topical carrier within which the N-acetylcysteine and odor masking material are incorporated. Concentrations of the topical carrier can vary with the carrier selected and the intended concentrations of the essential and optional components.

Suitable topical carders for use in the compositions include conventional or otherwise known carriers that are pharmaceutically acceptable for application to human skin. The topical carrier should also be physically and chemically compatible with the essential components described herein, or should not otherwise unduly impair aesthetics, odor masking properties, or other use benefits associated with the compositions of the present invention.

Preferred topical carders include emulsion systems such as oil-in-water emulsions, water-in-oil emulsions, and water-in-silicone emulsions, wherein substantially all of the N-acetylcysteine distributes into the aqueous phase and substantially all of the odor masking materials distribute into the hydrophobic or water-insoluble phase. The preferred topical carriers are described in detail hereinafter.

Water-in-Silicone Emulsion

Continuous Silicone Phase

A particularly preferred topical carrier for use in the compositions of the present invention are water-in-silicone emulsions comprising from about 1% to about 60%, preferably from about 5% to about 40%, more preferably from about 10% to about 20%, of a continuous silicone phase by weight of the topical carrier.

As used herein, "Liquid" refers to materials having a melting point of about 25° C. or less under about 1 atmosphere of pressure.

The Liquid organopolysiloxane can be selected from a wide variety of silicones spanning a broad range of volatilities and viscosities. Examples of organopolysiloxanes include polyalkylsiloxanes, cyclic polyalkylsiloxanes, and polyalkylarylsiloxanes. The polyalkylsiloxanes useful herein include, for example, polyalkylsiloxanes with viscosities of from about 0.5 to about 1,000,000 centistokes at 25° C. Such polyalkylsiloxanes correspond to the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also, useful are dimethicones having pendant alkyl groups ranging from C2 to about C30, these materials can be designated by the formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cycloxhethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

Aqueous Dispersed Phase

The preferred water-in-silicone emulsions comprise from about 30% to about 90%, preferably from about 50% to about 85%, most preferably from about 70% to about 80%, of a dispersed aqueous phase by weight of the topical carrier. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase.

As described hereinbefore, substantially all of the N-acetylcysteine will distribute into this dispersed aqueous phase. Other water-soluble or dispersible materials may also be incorporated into the dispersed aqueous phase.

Emulsifier for Dispersing the Phases

The preferred water-in-silicone emulsions comprise from about 0.1% to about 10%, preferably from about 0.5% to about 7.5%, more preferably from about 1% to about 5%, of an emulsifier for dispersing the discontinuous aqueous phase into the continuous silicone phase (percentages by weight of the topical carrier).

A wide variety of emulsifying agents can be employed herein to form the preferred water-in-silicone emulsion. Mixtures of emulsifying agents are also useful. These emulsifiers include those selected from the group consisting of silicone emulsifiers, non-silicon-containing emulsifiers, and mixtures thereof. Preferably these emulsifiers have an HLB value of less than about 14, more preferably from about 2 to about 14, and most preferably from about 4 to about 14. It is found that emulsifiers having an HLB value outside of these ranges can be utilized if they are used in combination with other emulsifiers, so to achieve an effective weighted average HLB for the combination that falls within the ranges described in the previous sentence. The abbreviation, "HLB," stands for hydrophilic lipophilic balance. The HLB system is well known to one of ordinary skill in the art and is described in detail in "The HLB System, A Time-Saving Guide to Emulsifier Selection," ICI Americas Inc., August 1984, which is incorporated herein by reference in its entirety.

A wide variety of silicone emulsifiers are useful herein. These silicon emulsifier are typically organically modified organopolysiloxanes. These materials are also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e. compounds which contain pendent C2–C30 pendant side chains. Still other useful dimethicone copolyols include materials having various cationic, anionic, amphoteric, and zwiterionic pendant moieties.

These dimethicone copolyols useful herein can be described by the following general structure:

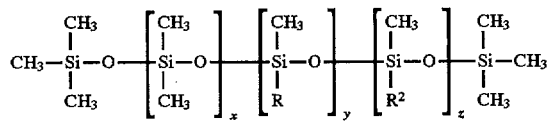

wherein R is C1–C30 straight, branched, or cyclic alkyl and $R^2$ is selected from the group consisting of

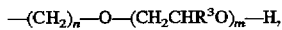

and

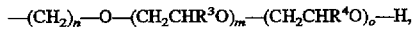

wherein n is an integer from 3 to about 10; $R^3$ and $R^4$ are selected from the group consisting of H and C1–C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

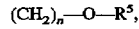

wherein $R^5$ is a cationic, anionic, amphoteric, or zwiterionic moiety;

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant caxboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Coming Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the trade name ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemthicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993, which is incorporated by reference herein in its entirety.

The dimethicone copolyol emulsifiers useful herein are further described in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," *Cosmetics & Toiletries*, vol. 110, pp. 91–100, March 1995; M. E. Carlotti et at., "Optimization of W/O-S Emulsions And Study Of The Quantitative Relationships Between Ester Structure And Emulsion Properties," *J. Dispersion Science And Technology*, 13(3), 315–336 (1992); P. Hameyer, "Comparative Technological Investigations of Organic and Organosilicone Emulsifiers in Cosmetic Water-in-Oil Emulsion Preparations," *HAPPI* 28(4), pp. 88–128 (1991); J. Smid-Korbar et at., "Efficiency and usability of silicone surfactants in emulsions," *Provisional Communication, International Journal of Cosmetic Science*, 12, 135–139 (1990); and D. G. Krzysik et al., "A New Silicone Emulsifier For Water-in-Oil Systems," *Drug and Cosmetic Industry*, vol. 146(4) pp. 28–81 (April 1990); which have already been incorporated by reference herein in their entirety.

Among the non-silicon-containing emulsifiers useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkyl phosphates, polyoxyalkylene fatty ether phosphates, fatty acid amides, acyl lactylates, soaps, and mixtures thereof. See McCutcheon's, *Detergents and Emulsifiers*, North American Edition (1986), published by Allured Publishing Corporation; U.S. Pat. No. 5,011,681 to Ciotti et at., issued Apr. 30, 1991; U.S. Pat. No. 4,421,769 to Dixon et at., issued Dec. 20, 1983; and U.S. Pat. No. 3,755,560 to Dickert et at., issued Aug. 28, 1973; these four references are incorporated herein by reference in their entirety.

Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaturate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Oil-in-Water Emulsions

Other preferred topical carders include oil-in-water emulsions. An especially preferred oil-in-water emulsion is described in detail hereinafter.

1. Structuring Agent

A preferred oil-in-water emulsion comprises a structuring agent to assist in the formation of a liquid crystalline gel network structure. Concentrations of such structuring agents are from about 1% to about 20%, preferably from about 1% to about 10%, more preferably from about 3% to about 9% by weight of the topical carrier.

Suitable structuring agents are those selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.

Preferred structuring agents include stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof. Most preferred is steareth-2, available under the tradename of Brij® 72 from ICI Americas.

2. Hydrophilic Surfactant

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Suitable surfactants include any of a wide variety of known cationic, anionic, zwitterionic, and amphoteric surfactants. See McCutcheon's, *Detergents and Emulsifiers*, North American Edition (1986), published by Allured Publishing Corporation; U.S. Pat. No. 5,011,681; U.S. Pat. No. 4,421,769; and U.S. Pat. 3,755,560; these four references are incorporated herein by reference in their entirety.

The exact surfactant chosen will depend upon the pH of the composition and the other components present.

Preferred are cationic surfactants, especially dialkyl quaternary ammonium compounds, examples of which are described in U.S. Pat. No. 5,151,209; U.S. Pat. No. 5,151, 210; U.S. Pat. No. 5,120,532; U.S. Pat. No. 4,387,090; U.S. Pat. No. 3,155,591; U.S. Pat. No. 3,929,678; U.S. Pat. No. 3,959,461; McCutcheon's, *Detergents & Emulsifiers*, (North American edition 1979) M. C. Publishing Co.; and Schwartz, et al., *Surface Active Agents, Their Chemistry and Technology*, New York: Interscience Publishers, 1949; which descriptions are incorporated herein by reference. The cationic surfactants useful herein include cationic ammonium salts such as those having the formula:

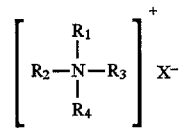

wherein $R_1$, is an alkyl group having from about 12 to about 30 carbon atoms, or an aromatic, aryl or alkaryl groups having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et at., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 careen atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

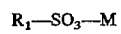

$$R_1-SO_3-M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[(CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dedecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

3. Water

The preferred oil-in-water emulsion comprises from about 25% to about 98%, preferably from about 65% to about 95%, more preferably from about 70% to about 90% water by weight of the topical carrier.

Optional Components

A wide variety of optional components can be employed in the topical skin compositions herein, provided that such optional components are physically and chemically comparable with the essential components described herein, or do not otherwise unduely impair aesthetics, stability or use benefits of the composition.

Zinc Salts

The compositions of the present invention may further comprise chelating agents capable of complexing with thiol-containing compounds to provide odor control prior to topical application. Concentrations of the chelating agents range from bout 0.001% to about 10%, preferably from about 0.01% to about 5%, more preferably from about 0.1% to about 0.5%, by weight of the composition.

Preferred chelating agents include the zinc salts, examples of which include zinc acetate, zinc acetate hydrates such as zinc acetate-2-water, zinc aluminum oxide complexes such as gahnite, zinc dime, zinc antimonide, zinc bromate hydrates such as zinc bromate-6-water, zinc bromide, zinc carbonates such as zincspar and smithsonite, zinc chlorate hydrates such as zinc chlorate-4-water, zinc chloride, zinc diamine dichloride, zinc citrate, zinc chromate, zinc dichromate, zinc diphosphate, zinc hexacyanofluoride ferrate (H), zinc fluoride, zinc fluoride hydrates such as zinc fluoride-4-water, zinc formate, zinc formate hydrates such as zinc formate-2-water, zinc hydroxide, zinc iodate, zinc iodate hydrates such as zinc iodate-2-water, zinc iodide, zinc iron oxide complexes, zinc nitrate hydrates such as zinc nitrate-6-water, zinc nitride, zinc oxalate hydrates such as zinc oxalate-2-water, zinc oxides such as zincite, zinc perchlorate hydrates such as zinc perchlorate-6-water, zinc permanganate hydrates such as zinc permanganate-6-water, zinc peroxide, zinc p-phenolsulfonate hydrates such as zinc p-phenosulfonate-8-water, zinc phosphate, zinc phosphate hydrates such as zinc phosphate-4-water, zinc phosphide, zinc propionate, zinc selenate hydrates such as zinc selenate-5-water, zinc selenide, zinc silicates such as zinc silicate (2) and zinc silicate (4), zinc silicon oxide water complexes such as hemimorphite, zinc hexafluorosilicate hydrates such as zinc hexafluorosilicate-6-water, zinc stearate, zinc sulfate, zinc sulfate hydrates such as zinc sulfate-7-water, zinc sulfide, zinc sulfite hydrates such as zinc sulfite-2-water, zinc telluride, zinc thiocyanate, zinc (II) salts of N-acetyl L-cysteine, and mixtures thereof.

Especially preferred zinc salts include zinc titrate, zinc oxide, zinc chloride, zinc acetate, zinc stearate, zinc sulfate, and mixtures thereof.

It has also been found that zinc citrate is especially effective in providing odor control prior to topical application. It is believed that the zince citrate, as well as the other zinc salts, act as chelating agents to bind thiol-containing compounds within the composition. This results in improved stability of the N-acetylcysteine and reduced malodor formation.

Sunscreens, Artificial Tanning Agents, and Skin Lightening Agents

Sunscreening agents may also be used in the topical compositions of the present invention at concentrations generally ranging from about 0.5% to about 20% by weight of the composition. Examples of suitable sucreening agents are described in U.S. Pat. No. 5,087,445; U.S. Pat. No. 5,073,372; U.S. Pat. No. 5,073,371; U.S. Pat. No. 4,937,370; U.S. Pat. No. 4,999,186; and Segarin, et al., at Chapter VIII, pages 189 et seq., of *Cosmetics Science and Technology*, which descriptions are incorporated herein by reference.

Specific examples of suitable sunscreens include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N- (2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Sunless tanning agents may also be used in the compositions, examples of which include dihydroxyacetone, glyceraldehyde, indoles and their derivatives, phospha-DOPA, tyrosine, and tyrosine esters such as ethyl tyrosinate. Skin bleaching (or lightening) agents may also be used, including but not limited to hydroquinone, ascorbic acid, kojic acid and sodium metabisulfite.

Humectants, Moisturizers, and Skin Conditioners

The compositions of the present invention may further comprise a humectant, moisturizing agent or skin conditioning agent. A variety of these materials can be employed and each can be present at a level of from about 0.1% to about 20%, more preferably from about 1% to about 10%, and most preferably from about 2% to about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also useful herein are the propoxylated glycerols described in U.S. Pat. No. 4,976,953, which is description is incorporated herein by reference.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean off fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et at., issued Apr. 26, 1994; U.S. Pat. No. 5,306,515, to Letton et at., issued Apr. 26, 1994; U.S. Pat. No. 5,305,514, to Letton et at., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Other Optional Components

The compositions of the present invention may further comprise other optional components, including absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, flagrance components, humectants, opacifying agents, pH adjusters, plasticizers, preservatives, propellants, reducing agents, additional skin-conditioning agents, skin protectants, solvents, suspending agents, ultra-violet light absorbers, emulsifiers, solubilizing agents, sequestrants, perfume chemicals other than those described herein for use in the odor masking material, and the like.

Nonlimiting examples of these additional components cited in the CTFA Cosmetic Ingredient Handbook, as well as other materials useful herein, include the following: water-soluble vitamins and derivatives thereof [e.g., vitamin C]; anti-oxidants; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; antioxidants; chelators and sequestrants. Also useful are crosslinked and noncrosslinked nonionic and cationic polyacrylamides [e.g., Salcare SC92 which has the CTFA designation polyquaternium 32 (and) mineral oil, and Salcare SC 95 which has the CTFA designation polyquaternium 37 (and) mineral oil (and) PPG-1 trideceth-6, and the nonionic Seppi-Gel polyacrylamides available from Seppic Corp.]. Also useful are crosslinked and uncrosslinked carboxylic acid polymers and copolymers such as those containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (examples useful herein include the carbomers, which are homopolymers of acrylic acid crosslinked with allyl ethers of sucrose or pentaerytritol and which are available as the Carbopol® 900 series from B.F. Goodrich, and copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol, these copolymers being known as acrylates/C10-30 alkyl acrylate crosspolymers and are commercially available as Carbopol® 1342, Pemulen TR-1, and Pemulen TR-2, from B.F. Goodrich). These carboxylic acid polymers and copolymers are more fully described in U.S. Pat. No. 5,087,445, to Haffey et at., issued Feb. 11, 1992; U.S. Pat. No. 4,509,949, to Huang et at., issued Apr. 5, 1985; U.S. Pat. No. 2,798,053, to Brown, issued Jul. 2, 1957; which are incorporated by reference herein. See also, CTFA International Cosmetic Ingredient Dictionary, fourth edition, 1991, pp. 12 and 80; which is also incorporated herein by reference. Also useful herein are aesthetic components such as fragrances, pigments, colorings, essential oils, skin senates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate and the like.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Each of the following formulations described in Examples I–IX is prepared by combining the listed components using conventional formulation and mixing techniques.

The odor masking materials referred to below in Examples I–IX are defined as follows:

Odor Masking Materials

| Perfume Chemical | Material I | Material II | Material III |
|---|---|---|---|
| Benzyl acetate | 31.5 | 15 | 18.5 |
| Benzyl butyrate | — | — | 0.7 |
| Benzyl propionate | 5 | 5 | 1 |
| Citronellol | 3 | — | 11.5 |
| Citronellyl acetate | 2 | 5 | 1 |
| Damascone Beta | .5 | — | .2 |
| Decyl aldehyde | — | — | 1 |
| Dihydro myrcenol | 4.5 | 10 | 5 |
| Geraniol | 5 | 10 | 3.5 |
| Geranyl acetate | 4 | 5 | 1 |
| Geranyl formate | — | — | 4.5 |
| Hexyl cinnamic aldehyde | 8 | 7 | 3.3 |
| Ionone Beta | 1.5 | — | — |
| Ionone Gamma Methyl | 2 | 1 | — |
| Lauric aldehyde | — | — | .5 |
| Linalyl acetate | 3 | 8 | 4 |
| Methyl anthranilate | — | — | .5 |
| P. T. Bucinal/Lilial | 1.0 | — | 5 |
| Phenyl ethyl acetate | 5 | 3 | 7 |
| Phenyl ethyl alcohol | 25 | 13 | 15 |
| Prenyl acetate | — | 2 | .8 |
| Terpineol | — | 3 | 2 |
| Verdox | — | 4 | 3 |
| Vertenex | — | 5 | 10 |
| Total | 100 | 100 | 100 |

Example I

Oil in Water Emulsion

| Component | wt % |
|---|---|
| PPG-15 Stearyl Ether | 3.25 |
| Glycerin | 3.0 |
| Stearyl Alcohol | 2.028 |
| N-Acetyl-L-Cysteine | 2.0 |
| Sodium Hydroxide (50% by weight aqueous solution) | 1.28 |
| Steareth-2 | 1.097 |
| Polyethylene | 1.0 |
| Dimethicone | 1.0 |
| Distearyl Dimethyl Ammonium Chloride | 0.95 |
| Cyclomethicone (and) Dimethiconol | 0.75 |
| Cetyl Alcohol | 0.559 |
| Benzyl Alcohol | 0.5 |
| Steareth-21 | 0.366 |
| Methyl Paraben | 0.25 |
| Behenyl Alcohol | 0.221 |
| Odor masking material (Material I) | 0.1 |
| Water | qs |

Example II

Water in Silicone Emulsion

| Component | wt % |
|---|---|
| Cyclomethicone | 15 |
| Ethanol | 3 |
| Glycerin | 3 |
| Polyglyceryl-4 Isostearate (and) Cetyl Dimethicone Copolyol (and) Hexyl Laurate | 2.5 |
| Cyclomethicone (and) Dimethicone Copolyol | 2.5 |
| Hexylene Glycol | 2 |
| N-Acetyl-L-Cysteine | 2 |
| Zinc Citrate | 1 |
| Sodium Hydroxide (50% by weight aqueous solution) | 0.95 |
| Tetrasodium EDTA | 0.5 |
| Benzyl Alcohol | 0.3 |
| Methyl Paraben | 0.2 |
| Citric Acid | 0.2 |
| Odor masking material (Material I) | 0.2 |
| Water | qs |

Example III

Aqueous Gel

| Component | wt % |
|---|---|
| Glycerin | 3 |
| Hexylene Glycol | 2 |
| N-Acetyl-L-Cysteine | 2 |
| Dimethiconol | 1 |
| Carbopol 980 | 1 |
| Zinc Citrate | 1 |
| Sodium Hydroxide | 0.9 |
| Benzyl Alcohol | 0.5 |
| Methyl Paraben | 0.25 |
| Citric Acid | 0.2 |
| Odor masking material (Material I) | 0.2 |
| Disodium EDTA | 0.1 |
| Keltrol T | 0.03 |
| Water | qs |

Examples IV–VI

The compositions described in each of Examples I–III are each reformulated, all ingredients being the same except that Material II is used as the odor masking material rather than Material I.

Examples VII–IX

The compositions described in each of Examples I–III are each reformulated, all ingredients being the same except that Material III is used as the odor masking material rather than Material I.

Each composition described in Examples I–IX when applied topically to human skin fails to emit excessive malodors associated with thiol or hydrogen sulfide materials, and each composition when applied topically applied improves the appearance of the skin.

What is claimed is:

1. A topical composition comprising:
  (a) from about 0.01% to about 50% by weight of a compound selected from the group consisting of N-acetylcysteine, derivatives of N-acetylcysteine, pharmaceutically-acceptable salts of N-acetylcysteine, pharmaceutically-acceptable salts of derivatives of N-acetylcysteine, and mixtures thereof;
  (b) from about 0.01% to about 0.5% by weight of an odor masking material selected to cover malodors associated with topical application of said compound (a) onto skin, wherein said odor masking material comprises the following perfume chemicals
    (i) from about 35% to about 95% by weight of aromatic ester, aliphatic ester or mixtures thereof, having a molecular weight of from about 120 to about 205;
    (ii) from about 4% to about 60% by weight of aromatic alcohol, aliphatic alcohol, or mixtures thereof, having a molecular weight of from about 110 to about 180;

(iii) from about 0.05% to about 20% by weight of aliphatic ketones having a molecular weight of less than about 210;

(iv) from about 0.1% to about 20% by weight of aromatic aldehydes, aliphatic aldehydes or mixtures thereof, having a molecular weight of from about 100 to about 225; and (v) not more than about 20% by weight of perfume chemicals selected from the group consisting of aromatic ether, aliphatic ether, aliphatic ester, aromatic ester, or mixtures thereof, having a molecular weight of at least about 210; and (c) a cosmetically acceptable topical carrier.

2. The composition of claim 1, wherein the odor masking material comprises (i) from about 40% to about 85% by weight of aromatic ester, aliphatic ester or mixtures thereof, having a molecular weight of from about 120 to about 205;

(ii) from about 10% to about 50% by weight of aromatic alcohol, aliphatic alcohol, or mixtures thereof, having a molecular weight of from about 110 to about 180;

(iii) from about 0.1% to about 15% by weight of aliphatic ketones having a molecular weight of less than about 210;

(iv) from about 0.2% to about 15% by weight of aromatic aldehydes, aliphatic aldehydes or mixtures thereof, having a molecular weight of from about 100 to about 225;

(v) not more than about 10% by weight of perfume chemical selected from the group consisting of aromatic ether, aliphatic ether, aliphatic ester, aromatic ester, or mixtures thereof, having a molecular weight of at least about 210.

3. The composition of claim 2 wherein the odor masking material comprises (i) from about 40% to about 85% by weight of aromatic ester, aliphatic ester or mixtures thereof, having a molecular weight of from about 150 to about 200;

(ii) from about 10% to about 50% by weight of aromatic alcohol, aliphatic alcohol, or mixtures thereof, having a molecular weight of from about 120 to about 160;

(iii) from about 0.1% to about 15% by weight of aliphatic ketones having a molecular weight of from about 160 to about 200;

(iv) from about 0.2% to about 15% by weight of aromatic aldehydes, aliphatic aldehydes or mixtures thereof, having a molecular weight of from about 130 to about 220; and (v) not more than about 5% by weight of perfume chemicals selected from the group consisting of aromatic ether, aliphatic ether, aliphatic ester, aromatic ester, or mixtures thereof, having a molecular weight of at least about 210.

4. The composition of claim 2 wherein said compound (a) is N-acetyl-L-cysteine.

5. The composition of claim 4 wherein said composition comprises from about 0.02% to about 0.3% by weight of the odor masking material.

6. The composition of claim 5 wherein said composition comprises from about 0.03% to about 0.2% by weight of the odor masking material and from about 0.1% to about 10% by weight of N-acetyl-L-cysteine.

7. The composition of claim 4 wherein the perfume chemicals are selected from the group consisting of: 2,6,10-trimethyl-9-undecen-1-al; 3-methyl- 1 -butanol acetate; 4-methoxy benzaldehyde; benzaldehyde; benzyl acetate; benzyl butyrate; benzyl propionate; 1-(2,6,6-trimethyl-1-cyclohexen-1-yl)-2-butene-1-one; beta, gamma-hexenyl salicylate; 3,7-dimethyl-6-octenol; 3,7-dimethyl-6-octen-1-yl acetate; 3,7-dimethyl-2,6-octadienenitrile; 2-methyl-3-(para iso propyl phenyl)propionaldehyde; decyl aldehyde; 1-(2,6,6-trimethyl-3-cyclo-hexen-1-yl)-2-buten-1-one; 3-methylene-7-methyl octan-7-ol; ethyl vanillin; 3-(3-isopropylphenyl) butanal; 3,7-dimethyl-2,6-octadien-1-ol; 3,7-dimethyl-2,6-octadien-1-yl acetate; trans 3,7-dimethyl-2,6-octadienyl formate; 3,7-dimethyl-2,6-octadienenitrile; alpha-methyl-3,4, (methylenedioxy) hydrocinnamaldehyde; heliotropin; alpha-n-hexyl cinnamic acid; hydroxycitronellal; 4-(2,6,6-trimethyl-1-cyclohexenyl-1-yl)-3-buten-2-one; 4-(2,6,6-trimethyl-1-cyclohexen-1-yl)-3-butene-2-one; acetyl di-isoamylene; lauric aldehyde; 3-hydroxy-3,7-dimethyl- 1,6-octadiene acetate; linalyl-n-butyrate; 3,7-dimethyl- 1,6-octadien-3-yl propionate; 4-(4-hydroxy-4-methyl-pentyl) 3-cylcohexene-1-carboxaldehyde; methyl-2-aminobenzoate; methyl nonyl acetaldehyde; 2-methyl-3 (para tert butylphenyl) propionaldehyde; 1-oxo-2-phenylethane; phenyl acetaldehyde dimethyl acetal; phenyl ethyl acetate; phenyl ethyl alcohol; 2-methylbuten-2-ol-4-acetate; para-menth-1-en-8-ol, para-menth-1-en-1-ol; undecanal; undecylenic aldehyde; 4-hydroxy-3-methoxybenzaldehyde; 2-tert-butyl cyclohexyl acetate; 4-tertiary-butyl cyclohexyl acetate; and mixtures thereof.

8. The composition of claim 1 wherein the cosmetically acceptable topical carrier is selected from the group consisting of an oil-in-water emulsion, a water-in-oil emulsion, a water-in-silicone emulsion, and an aqueous gel.

9. The composition of claim 1 wherein said composition further comprises from about 0.001% to about 10% by weight of a zinc salt.

10. The composition of claim 9 wherein the zinc salt is selected from the group consisting of zinc titrate, zinc oxide, zinc stearate, zinc sulfate, zinc chloride, zinc acetate, and mixtures thereof.

11. The composition of claim 10 wherein the zinc salt is zinc citrate.

12. A topical composition comprising:

(a) from about 0.1% to about 10% by weight of a N-acetyl-L-cysteine;

(b) from about 0.02% to about 0.3% by weight of an odor masking material selected to cover malodors associated with topical application of the N-acetyl-L-cysteine onto skin, wherein said odor masking material comprises the following perfume chemicals (i) from about 40% to about 85% by weight of aromatic ester, aliphatic ester or mixtures thereof, having a molecular weight of from about 120 to about 205;

(ii) from about 10% to about 50% by weight of aromatic alcohol, aliphatic alcohol, or mixtures thereof, having a molecular weight of from about 110 to about 180;

(iii) from about 0.1% to about 15% by weight of aliphatic ketones having a molecular weight of less than about 210;

(iv) from about 0.2% to about 15% by weight of aromatic aldehydes, aliphatic aldehydes or mixtures thereof, having a molecular weight of from about 100 to about 225;

(v) not more than about 5% by weight of perfume chemicals selected from the group consisting of aromatic ether, aliphatic ether, aliphatic ester, aromatic ester, or mixtures thereof, having a molecular weight of at least about 210;

(b) from about 0.001% to about 10% by weight of a zinc citrate; and (c) a cosmetically acceptable topical carrier selected from the group consisting of oil-in-water emulsions and water-in-silicone emulsions.

13. A topical composition comprising:

(a) from about 0.01% to about 50% by weight of a compound selected from the group consisting of N-acetylcysteine, derivatives of N-acetylcysteine, pharmaceutically-acceptable salts of N-acetylcysteine, pharmaceutically-acceptable salts of derivatives of N-acetylcysteine, and mixtures thereof;

(b) from about 0.001% to about 10% by weight of zinc citrate; and (c) a cosmetically acceptable topical carrier.

14. The composition of claim 13 wherein said composition comprises from about 0.01% to about 5% by weight of the zinc citrate.

15. The composition of claim 14 wherein said composition comprises from about 0.1% to about 0.5% by weight of the zinc citrate.

16. The composition of claim 13 wherein said compound (a) is N-acetyl-L-cysteine.

17. The composition of claim 16 wherein said composition comprises from about 0.1% to about 10% by weight of the N-acetyl-L-cysteine.

18. The composition of claim 17 wherein the topical carrier is selected from the group consisting oil-in-water emulsion, water-in-oil emulsion, water-in-silicone emulsion and aqueous gel.

* * * * *

UNITED STATES PATENT AND TRADEMARK OFFICE
CERTIFICATE OF CORRECTION

PATENT NO. : 5,733,535
DATED : March 31, 1998
INVENTOR(S) : Judith Ann Hollingshead and Larry Richard Robinson It is certified that error appears in the above-indentified patent and that said Letters Patent is hereby corrected as shown below:

column 1, line 57 "maledor" should read --malodor--.

column 2, line 7 "mash" should read --masks--.

column 4, line 7 "aeceptable" should read --acceptable--.

column 6, line 41 "Perfume" should read --perfume--.

column 6, line 53 "carders" should read --carriers--.

column 6, line 61 "carders" should read --carriers--.

column 7, line 9 "Liquid" should read --liquid--.

column 7, line 12 "Liquid" should read --liquid--.

column 7, line 30 "Coming" should read --Corning-- at both occurrences.

column 7, line 35 "Coming" should read --Corning--.

column 7, line 54 "cycloxhethicones" should read --cyclomethicones--.

column 7, lines 60-61 "Coming" should read -- Corning--.

column 7, line 64 "Coming" should read --Corning--.

column 8, line 23 "Coming" should read --Corning--.

column 9, line 6 "silicon emulsifier" should read --silicone emulsifiers--.

column 10, line 4 "caxboxylate" should read --carboxylate--.

column 10, line 10 "Coming" should read --Corning--.

column 10, line 36 "et at." should read --et al.--.

column 10, line 43 "et at." should read --et al.--.

column 10, line 63 "et at." should read --et al.--.

column 10, line 64 "et at." should read --et al.--.

column 10, line 65 "et at." should read --et al.--.

UNITED STATES PATENT AND TRADEMARK OFFICE
CERTIFICATE OF CORRECTION

PATENT NO. : 5,733,535

DATED : March 31, 1998

INVENTOR(S) : Judith Ann Hollingshead and Larry Richard Robinson

It is certified that error appears in the above-indentified patent and that said Letters Patent is hereby corrected as shown below:

column 11, line 9 "monolaturate" should read --monolaurate--.

column 11, line 15 "carders" should read --carriers--.

column 13, line 66 "et at." should read --et al.--.

column 14, line 15 "careen" should read --carbon--.

column 14, line 60 "dedecylaminopropane" should read --dodecylaminopropane--.

column 15, line 12 "165P" should read --16SP--.

column 15, lines 42-43 "comparable" should read --compatable--.

column 15, line 57 "zinc dime" should read --zinc diamine--.

column 15, lines 62-63 "ferrate(H)" should read -- ferrate(II) --.

column 16, line 17 "titrate" should read --citrate--.

column 17, line 22 "soybean off" should read --soybean oil--.

column 17, line 51 "et at." should read --et al.--.

column 17, line 52 "et at." should read --et al.--.

column 17, line 53 "et at." should read --et al.--.

column 18, line 1 "flagrance" should read --fragrance--.

column 18, line 44 "et at." should read --et al.--.

column 18, line 45 "et at." should read --et al.--.

column 22, line 36 "titrate" should read --citrate--.

Signed and Sealed this

Fourteenth Day of July, 1998

*Attest:*

BRUCE LEHMAN

*Attesting Officer*     Commissioner of Patents and Trademarks